US011967247B2

(12) United States Patent
Hargrove et al.

(10) Patent No.: US 11,967,247 B2
(45) Date of Patent: Apr. 23, 2024

(54) PROSTHETIC VIRTUAL REALITY TRAINING INTERFACE AND RELATED METHODS

(71) Applicant: Rehabilitation Institute of Chicago, Chicago, IL (US)

(72) Inventors: Levi J. Hargrove, Chicago, IL (US); Richard B. Woodward, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 17/063,217

(22) Filed: Oct. 5, 2020

(65) Prior Publication Data

US 2021/0049928 A1 Feb. 18, 2021

Related U.S. Application Data

(62) Division of application No. 15/954,417, filed on Apr. 16, 2018, now Pat. No. 10,796,599.

(Continued)

(51) Int. Cl.
*G09B 19/00* (2006.01)
*A61B 5/00* (2006.01)
(Continued)

(52) U.S. Cl.
CPC .......... *G09B 19/003* (2013.01); *A61B 5/296* (2021.01); *A61B 5/389* (2021.01); *A61B 5/681* (2013.01);
(Continued)

(58) Field of Classification Search
CPC .... G09B 19/003; G16H 20/30; A61B 5/0488; A61B 5/0492; A61B 5/681; A61B 5/6811;
(Continued)

(56) References Cited

U.S. PATENT DOCUMENTS 3,588,105 A * 6/1971 Donohoe ............. A63B 21/065 473/213
2009/0326406 A1* 12/2009 Tan ........................ G06F 3/017 341/20
(Continued)

FOREIGN PATENT DOCUMENTS

CN 102170825 A * 8/2011 ......... A61B 5/04888
CN 103892945 A 7/2014
JP 2005000389 A * 1/2005

OTHER PUBLICATIONS

Ortiz-Catalan, et al., BioPatRec: A modular research platform for the control of artificial limbs based on pattern recognition algorithms, Source Code for Biology and Medicine, Biomed Central Ltd, Lo, vol. 8, No. 1, Apr. 18, 2013.
(Continued)

*Primary Examiner* — Xuemei Zheng
*Assistant Examiner* — Nathan P Brittingham
(74) *Attorney, Agent, or Firm* — Polsinelli PC

(57) ABSTRACT

An apparatus comprising an arm band and an electromyographic (EMG) control module is disclosed. The apparatus includes an electromygraphic (EMG) control module configured to receive EMG information generated by an individual; identify a gesture class based on the EMG information, and train using the received EMG information and the gesture class. The gesture class corresponds to an intended gesture made by the individual.

16 Claims, 11 Drawing Sheets

Related U.S. Application Data

(60) Provisional application No. 62/485,885, filed on Apr. 14, 2017.

(51) Int. Cl.
*A61B 5/296* (2021.01)
*A61B 5/389* (2021.01)
*G06F 3/01* (2006.01)
*G06T 19/00* (2011.01)
*G16H 20/30* (2018.01)

(52) U.S. Cl.
CPC .......... *A61B 5/6811* (2013.01); *A61B 5/6824* (2013.01); *A61B 5/7405* (2013.01); *G06F 3/017* (2013.01); *G06T 19/003* (2013.01); *G16H 20/30* (2018.01)

(58) Field of Classification Search
CPC ..... A61B 5/6824; A61B 5/7405; G06F 3/017; G06T 19/003
See application file for complete search history.

(56) References Cited

U.S. PATENT DOCUMENTS

| | | | |
|---|---|---|---|
| 2009/0327171 A1* | 12/2009 | Tan | G06N 20/00 706/12 |
| 2014/0198035 A1* | 7/2014 | Bailey | G06F 3/0484 345/156 |
| 2014/0334083 A1* | 11/2014 | Bailey | G06F 1/1692 361/679.03 |
| 2015/0057770 A1* | 2/2015 | Bailey | G06F 3/015 700/83 |
| 2015/0135132 A1* | 5/2015 | Josephson | H04L 67/12 715/784 |
| 2016/0378193 A1* | 12/2016 | Camacho Perez | G06V 40/28 345/156 |
| 2017/0156965 A1* | 6/2017 | Geisinger | A61B 5/11 |

OTHER PUBLICATIONS

Ortiz-Catalan, et al., Treatment of phantom limb pain (PLP) based on augmented reality and gaming controlled by myoelectric pattern recognition: a case study of a chronic PLP patient, Frontiers in Neuroscience, vol. 8, Feb. 25, 2014.

\* cited by examiner

PROSTHETIC VIRTUAL REALITY TRAINING INTERFACE AND RELATED METHODS

RELATED APPLICATIONS

This application is a division of U.S. patent application Ser. No. 15/954,417, filed Apr. 16, 2018, which claims the benefit of U.S. Provisional Application No. 62/485,885, filed Apr. 14, 2017, each of which is incorporated by reference in its entirely herein and for all purposes.

STATEMENT OF GOVERNMENT SUPPORT

This invention was made with government support under W81XWH-15-2-0035 awarded by the United States Department of Defense. The government has certain rights in the invention.

FIELD

This disclosure generally relates to the fields of virtual reality (VR) and rehabilitation devices, in particular a rehabilitation VR system for therapeutic, training, and diagnostic purposes.

BACKGROUND

Limb loss and neurological disorders such as stroke, spinal cord injury, and cerebral palsy are significant medical conditions that can severely impact a person's quality of life and the life of their caregivers. Returning to a high level of ability post-injury requires specialized rehabilitation therapies and technologies. If prosthetics are needed, in order for those with these conditions to use the latest technology like myoelectric prostheses, extensive training is required. This training can be frustrating for a prosthesis user because the prosthesis does not work well at the start of training.

Electromyographic (EMG) signals are electrophysiological signals generated by a muscular contraction which propagates spatially through the body. The origin of the signal is the depolarization and repolarization of the muscle fiber cell membrane during a contraction which causes ionic currents to circulate creating measurable action potentials in the body. Individual muscle fibers are innervated in groups by a single nerve axon. This functional unit, consisting of the group of muscle fibers, nerve axon, and cell body of the nerve in the spinal cord is called a motor unit (MU). An MU generates a force twitch each time it is activated and an associated motor unit action potential (MUAP) is generated. The total force produced by the muscle is a superposition of all MU force twitches while the detected EMG is a superposition of all MUAPs and it can be detected at the skin's surface using surface electrodes or underneath the skin using invasive techniques. The nervous system has two general means to modulate the force of a muscle contraction: 1) by varying the number of recruited MUs, or 2) by modulating the firing rate of the recruited MUs. For either of these two conditions, the peak-to-peak amplitude and variance of the detected EMG increases in a roughly linear manner as force production increases. Thus, control signal(s) can be generated through a conscious voluntary effort by varying the intensity of a muscular contraction(s). This is true of healthy muscles, muscles atrophied through disuse, partially innervated muscles, and of normally innervated muscle remnants resulting from amputation.

SUMMARY

An apparatus comprising an electromyographic (EMG) control module may be configured to receive EMG information generated by an individual in response to a virtual reality display indicating a gesture class; train using the received EMG information and the gesture class; and after training, operate an assistive device.

The EMG control module may be configured to determine an intended gesture based on the EMG information; and output a gesture instruction associated with the intended gesture. The gesture instruction may be defined as a scalar value. The apparatus may further comprise a sensor system, the sensor system comprising a kinematic actuator for providing kinematic information about the individual to a virtual reality control module.

In response to the gesture instruction, the virtual reality display may display a virtual limb in a position reflecting the intended gesture. In response to the gesture instruction, the virtual reality display may shows a trace line originating at a limb avatar and terminating at a virtual target. An image representing the intended gesture may be displayed on the virtual target.

The EMG control module may be defined as a pattern recognition classifier. The EMG control module may comprise a plurality of gesture classes. The gesture classes may comprise a hand open class, a hand close class, a no motion class, a wrist rotation class, and a wrist extension/flexion class. The EMG signals generated by the individual may be generated by the individual's limb moving in more than one physical dimension. The EMG signals generated by the individual may be generated by the individual's limb moving in three physical dimensions.

The virtual limb may be displayed as a shooting device. The virtual reality display may be configured to display a virtual target. The virtual reality display may be configured to display a virtual target and the virtual target disappears if the virtual limb is not pointed at the virtual target after a predetermined period of time.

In an embodiment, an apparatus comprising an electromyographic (EMG) control module may be defined as a pattern recognition classifier, the EMG control module configured to receive EMG information generated by movement of an individual's limb in more than one physical dimension in response to a virtual reality display indicating a gesture class; and train using the received EMG information and the gesture class. Each class in the classifier may be trained using EMG information received from user movement in more than one physical dimension.

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

BRIEF DESCRIPTION OF THE DRAWINGS

The Detailed Description is described with reference to the accompanying figures. The same reference numbers in different figures indicate similar or identical items. References made to individual items of a plurality of items can use the same reference number.

Corresponding reference characters indicate corresponding elements among the view of the drawings. The headings used in the figures should not be interpreted to limit the scope of the claims.

DETAILED DESCRIPTION

A virtual reality (VR) interface for individuals is disclosed. The VR interface may provide individuals with physical disabilities self-administered and targeted rehabilitation within a home or clinical setting. In an embodiment, the VR interface may comprise an apparatus for control of the virtual reality device. The VR interface may further comprise independent virtual reality software for training, monitoring, or diagnostic purposes. The data from the VR interface may be analyzed and used to train a prosthesis to understand an individual's specific muscle movements. In other embodiments, the VR interface may be used in connection with VR systems for persons with neurological disorders such as amputations, stroke, spinal cord injury, or cerebral palsy. The foregoing and other aspects will become more apparent from the following detailed description when considered in conjunction with the accompanying drawings.

Figure 1A:
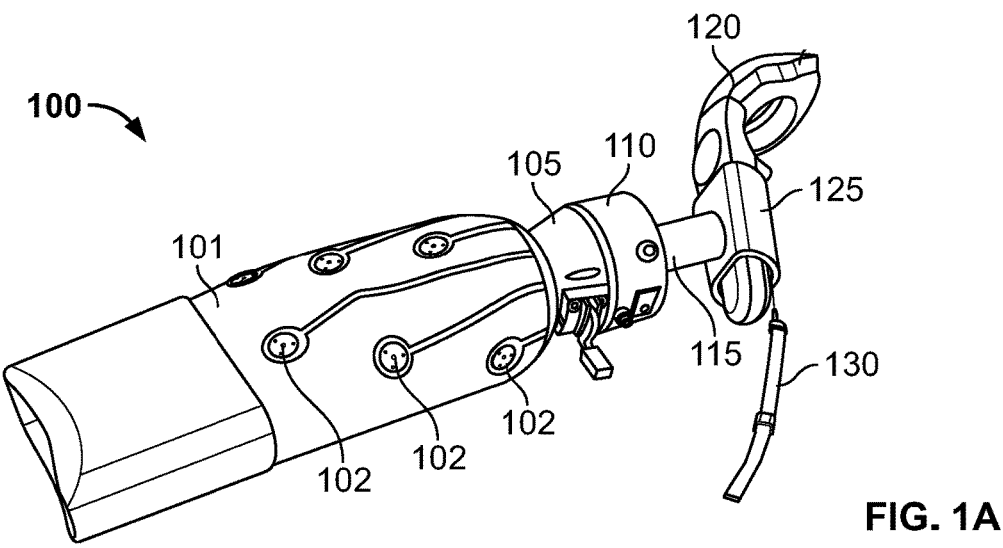
FIG. 1A is a perspective view of an exemplary virtual reality training device.

In one embodiment, a virtual reality (VR) training system is disclosed that provides enjoyable, self-administered, and targeted rehabilitation to upper-limb amputees within a home or clinical setting in order to increase the functional utilization and efficient training in the use of myoelectric prostheses in daily living activities. FIG. 1 displays an exemplary VR assistive device 100 comprising an instrumented liner 101, a magnetic electrical interface (MEI) 105, muscle computer interface (MCI) 110, stem 115, controller 120, controller support 125, and wrist strap 130. The controller 120 may be a controller used to operate a commercially available video game. Stem 115 and controller support 125 may be 3D printed or made of any other suitable material. The length of stem 115 may be adjusted to match the amputee's residual limb length. The liner 101 may be of the kind disclosed in U.S. Pat. No. 9,155,634 B2, titled Systems and methods of myoelectric control, incorporated by reference. MEI 105 may be of the kind disclosed in U.S. Patent Publication No. US-2016-0038314-AI, Magnetic Electrical Connector for Assistive Devices, incorporated by reference.

Figure 1B:
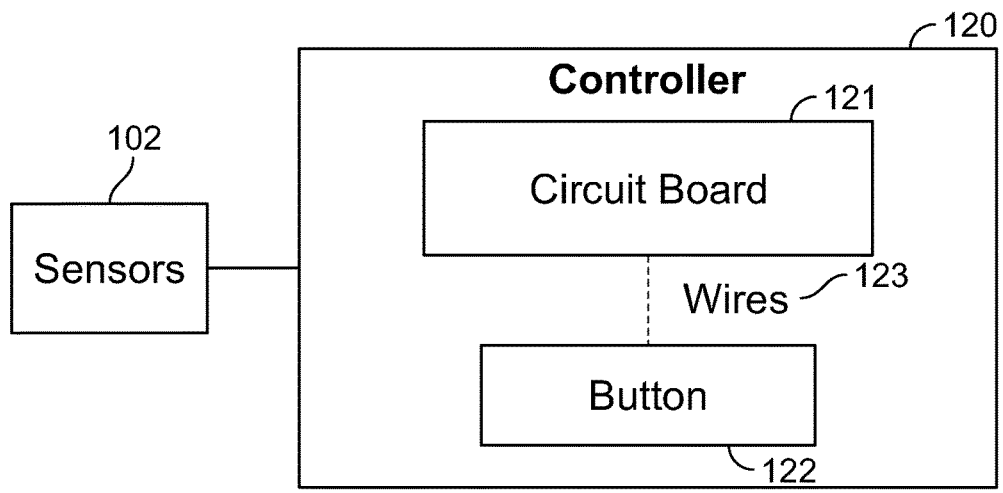
FIG. 1B is a block diagram of an exemplary controller and sensors of the exemplary virtual reality training device shown in FIG. 1A.

Controller 120 may allow both mechanical and electrical actuation. Controller support 125 may hold the controller 120 in place. The MCI 110 may comprise a power source such as a battery, an embedded control system, and an interface to the controller 120. The liner 101 comprises one or more sensors 102. The liner 101 is placed over a user's residual limb and the sensors 102 can receive electromyographic (EMG) information from the user's residual limb. The MCI 110 can process the EMG information from the sensors 102, interpret the information to determine user intention, and relay that information to the controller 120. The stem 115 may be made of ABS plastic or other suitable material. The stem 115 can serve as the interface between the MET 105 and controller support 125. The length of stem 115 can be customized based on the residual limb length to mimic the length of the user's non-amputated limb. This mechanism also has the ability to withstand and hold incremental weight, which can be used for training purposes in order to prepare the user for her prosthesis or other assistive device. In an embodiment, a controller 120 may be, for instance, a standard virtual reality controller, such as HTC Vive by HTC Corporation (New Taipei City, Taiwan, http://www.vive.com). FIG. 1B shows a representation of an exemplary controller 120. The controller 120 may be modified with an embedded circuit board 121. Input signals from the sensors 102 may be relayed through the embedded circuit board 121 and passed to the controller buttons 122 via wires 123 which may be soldered. The controller buttons 122 may comprise one or more physical buttons. A 3.3-volt signal (or signal of other appropriate voltage) can simulate the physical pressing of a controller button 122. This modification allows an electrical signal produced by contracting muscle (EMG) to engage or disengage a controller button 122 on the controller electronically. The EMG signal is received by at least one sensor 102, processed by the embedded circuit board 121, and used to simulate actuation of a controller button 122. Therefore, a controller button 122 may be triggered either mechanically (through typical interaction with the hand/fingers) or electronically (controlled via EMG and relayed through the embedded circuit board 121. In other embodiments, the controller buttons may be replaced with other types of actuators, such as physical switches. In other embodiments, the embedded circuit board may be located elsewhere than the controller.

The controller support 125 may be made of ABS plastic or any other suitable material. In an embodiment, the controller support 125 may be defined by a tube shape. The controller support 125 may hold a controller 120 at an angle, in order to mimic the correct orientation that a non-amputated hand would hold the controller. The wrist strap 130 is a vestige of the controller 120 and may not be needed by the user.

Figure 2:
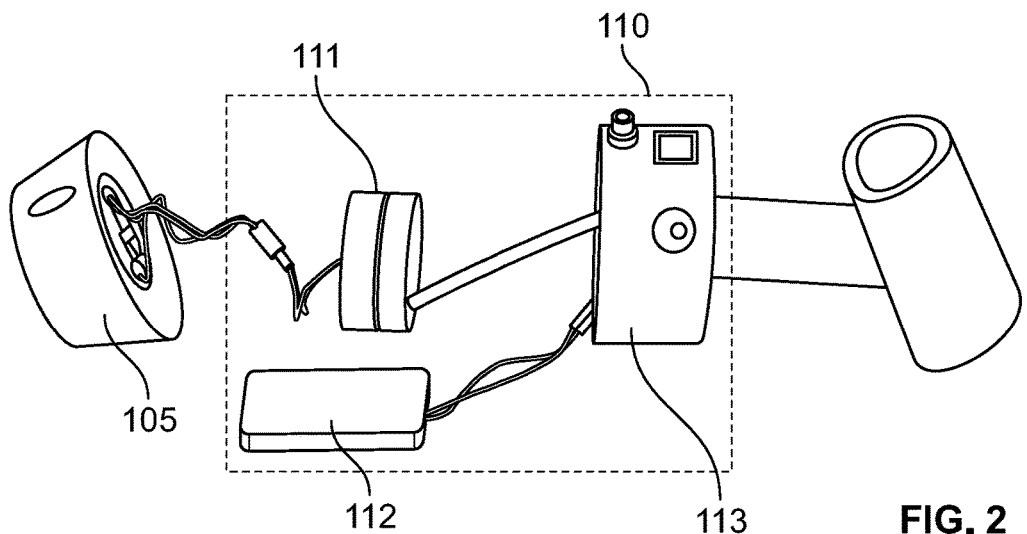
FIG. 2 is an exploded side view of portions of the exemplary virtual reality training device shown in FIG. 1A.
Figure 3:
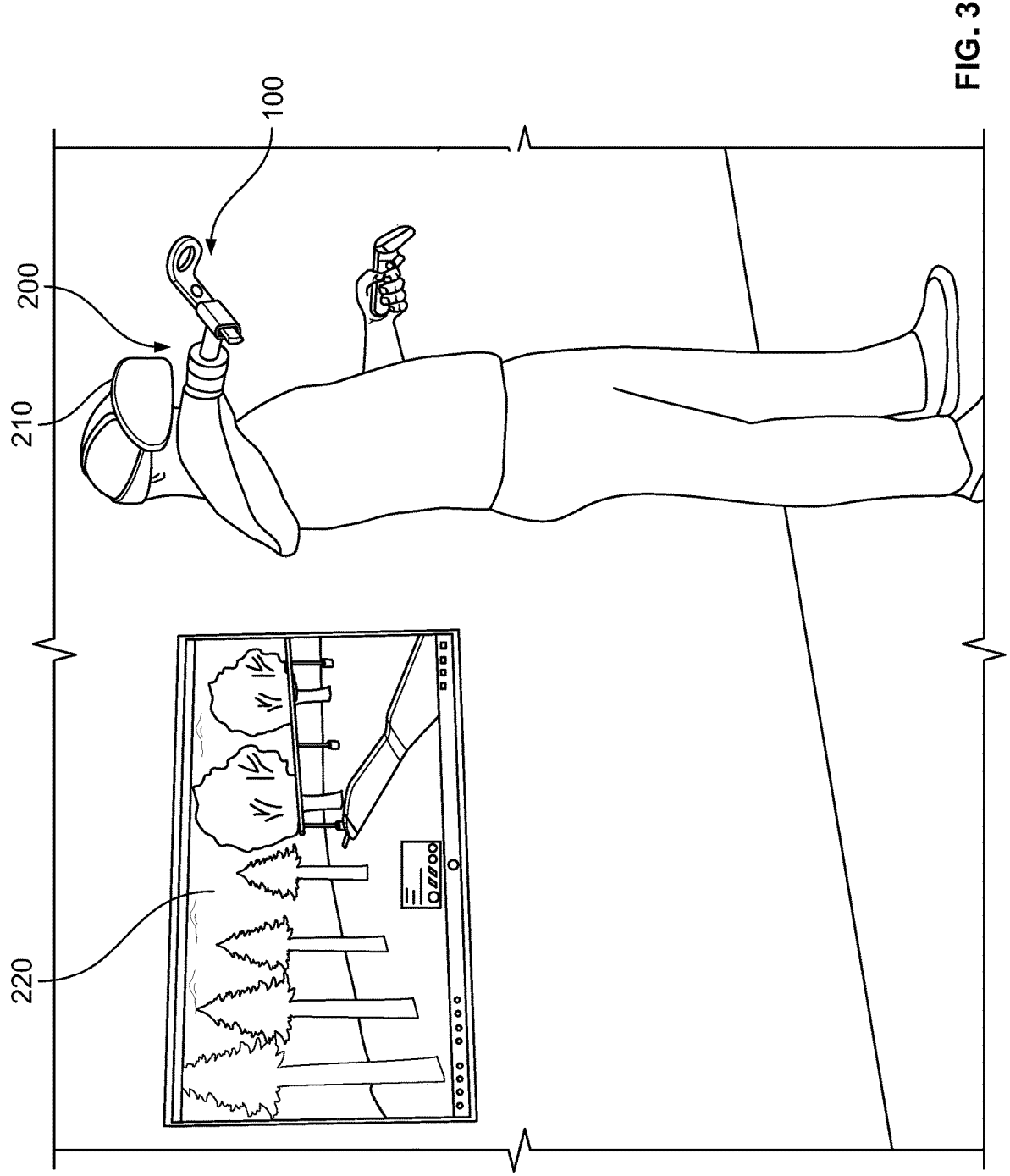
FIG. 3 is a representation of a person using the exemplary virtual reality training device shown in FIG. 1A in coordination with an exemplary VR interface.
Figure 4:
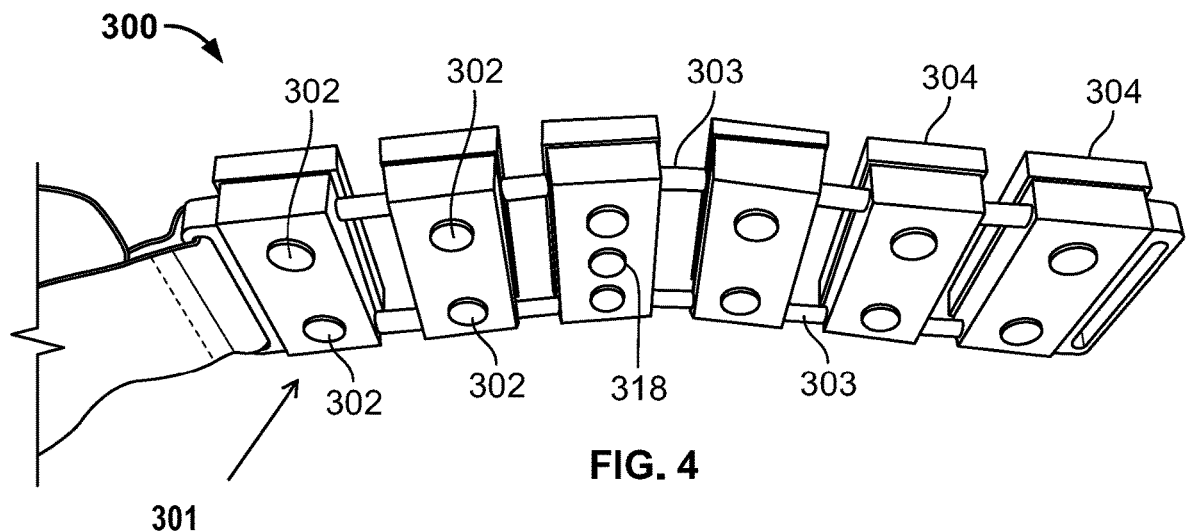
FIG. 4 shows an exemplary myoelectric arm band.

FIG. 2 shows an embodiment of the MEI 105 and the MCI 110 module, comprising a control unit 111, battery 112, and housing 113. FIG. 3 displays a person using an exemplary VR interface 200. The VR interface 200 may comprise an assistive device, such as VR assistive device 100. The VR interface may further comprise a VR display 210 that can be viewed by the user while she operates the VR assistive device 100. In the embodiment shown in FIG. 3, the VR display 210 is attached to the user's head. Other virtual reality displays may alternately be used. A display 220 also may be provided, to display the image being shown on the VR display 210 and viewed by the user of the system. The VR interface 200 allows a user with an amputation or other condition requiring a prosthesis, orthosis, or other assistive device to view a series of images that change depending at least in part on the action the user takes to move or otherwise operate the VR assistive device 100. For instance, the series of images may comprise a video game that is used to train the user in the operation of the VR assistive device 100. As shown in FIG. 3, the display 220 displays the same image that is displayed to the user on the VR display 210.

Figure 5:
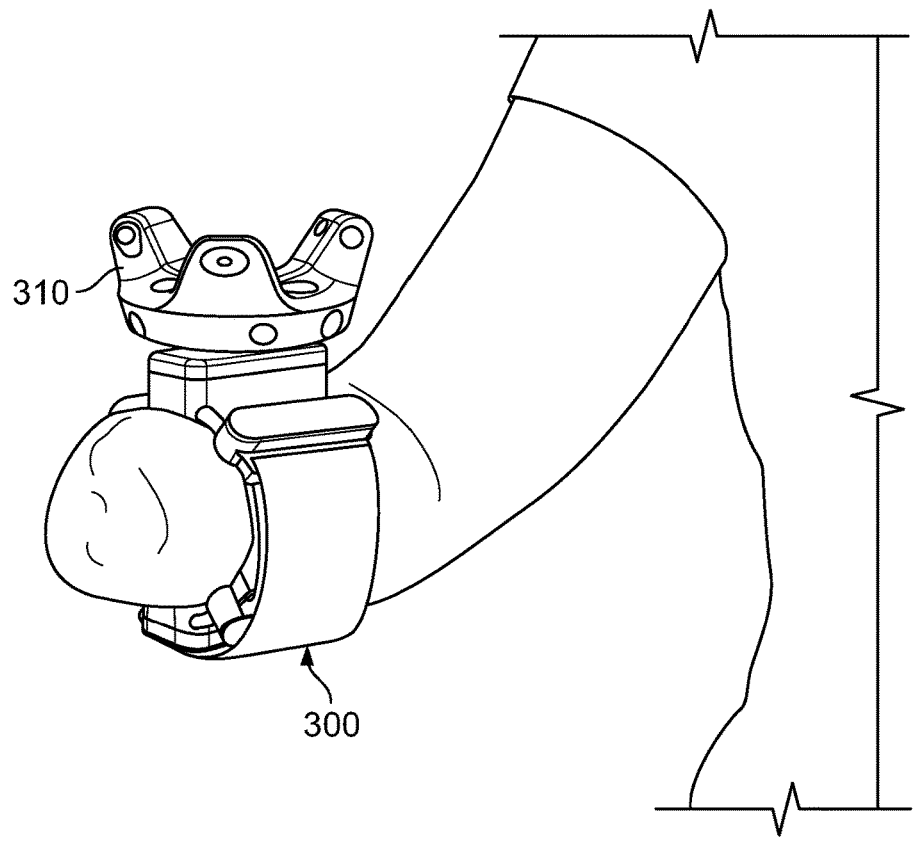
FIG. 5 shows the exemplary myoelectric arm band of FIG. 4 attached to the residual limb of a user.
Figure 6:
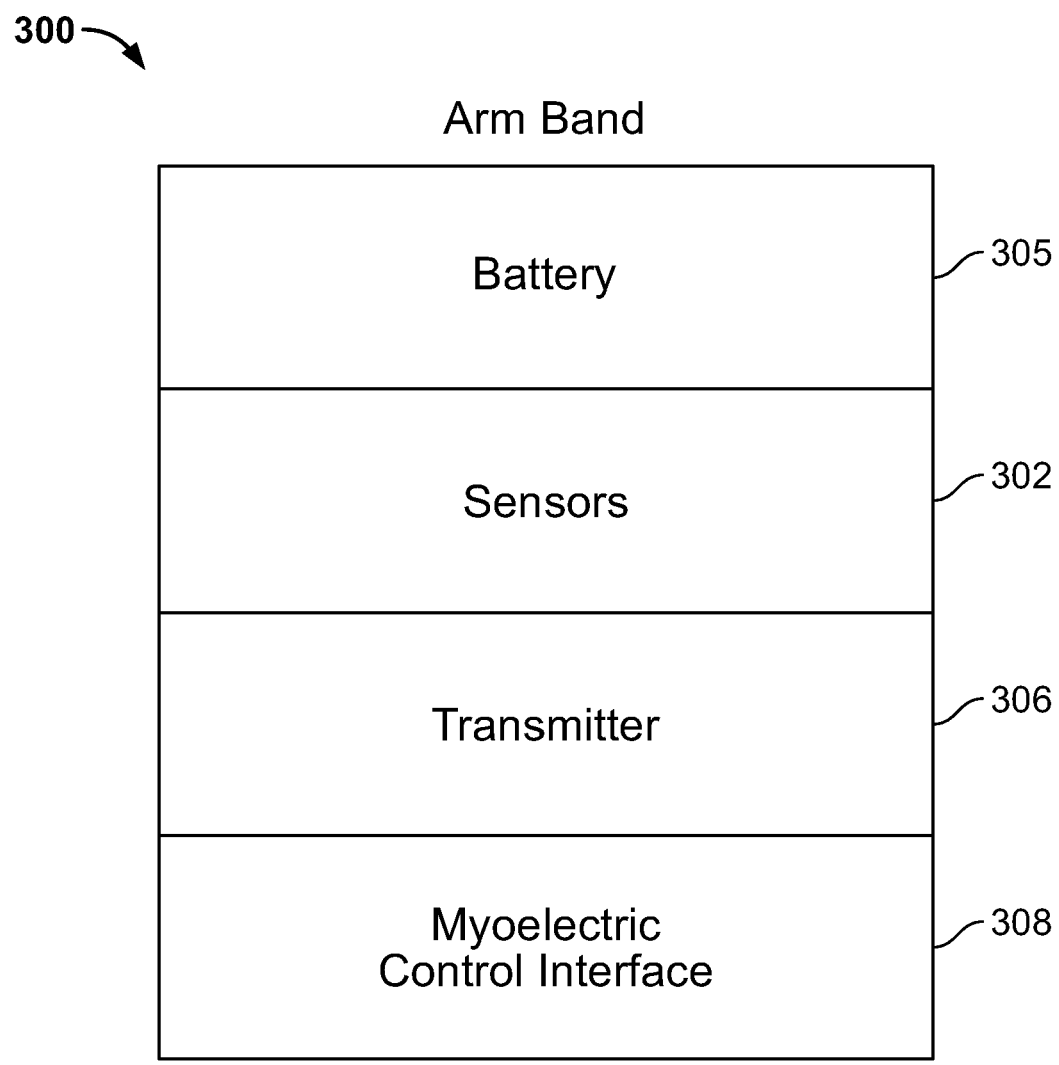
FIG. 6 is a block diagram of the exemplary arm band shown in FIG. 4.

In an embodiment, an arm band 300 may be used in lieu of the VR assistive device 100. The arm band 300 may comprise one or more sensors 302 provided in a housing 301. The housing 301 may comprise more than one housing element 304 which may be connected by flexible connectors 303. The arm band 300 may be wrapped around a residual limb as shown in FIG. 5. The housing elements 304 may be modified to weigh more or less in order to simulate the feeling of the assistive device that has been prescribed for the user. The armband 300 may have a wireless transmitter 306 that allows EMG information received by the sensors 302 to be transmitted wirelessly. The transmitter 306 may also transmit a gesture instruction produced by the myoelectric control interface 308. FIG. 6 shows a representation of the arm band 300 comprising sensors 302, a battery 305, a transmitter 306, and a myoelectric control interface 308. The myoelectric control interface 308 receives the EMG information from the sensors 302 and determines the likely gesture the user was attempting to make, based on user's muscle movement which generates EMG information received by the sensors 302.

The arm band 300 may comprise amplification and processing electronics. The electronics may be contained within the housing elements 304. For instance, a first housing element may contain an amplifier board and a second housing element may contain a processing board. Separate housing elements 304 may contain a battery. One housing element 304 may comprise a ground electrode. The electronics may be used to process EMG signals as is known in the art. The myoelectric control interface 308 is a type of EMG control module 420 (described below). The myoelectric control interface 308 may be defined as a pattern recognition classifier as described in further detail below.

Figure 7:
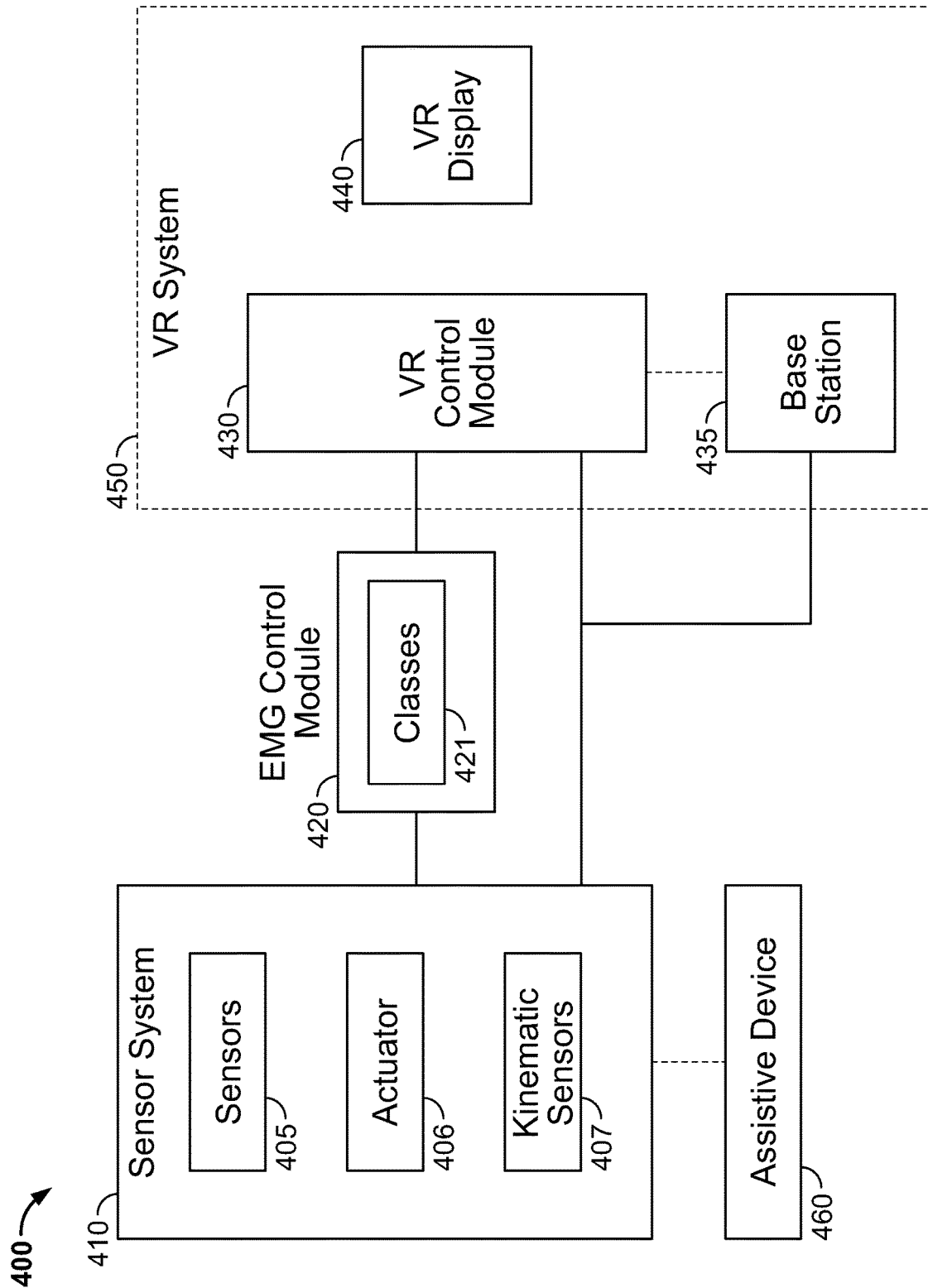
FIG. 7 is a block diagram of an exemplary interface.

More generally, FIG. 7 displays a representation of an interface 400. The interface 400 may comprise a sensor system 410 that comprises at least one EMG sensor 405. The sensor system 410 may comprise a physical actuator 406, such as a button, switch, touch-activated display, or the like. The sensor system 410 may also comprise one or more kinematic sensors 407 for determining the position, velocity, acceleration, or other kinematic characteristic of a portion of a user of the interface 400, such as the user's limb. Such characteristics may include, for example, gravitational position, inertial measurement, yaw, pitch, roll, or other kinematic characteristics. The sensor system 410 receives EMG information from a user and transmits it to an EMG control module 420. The sensor system 410 may additionally comprise amplifiers, filters, and other electronics systems known in the art for processing EMG signals and providing EMG information to a control module. The EMG control module 420 analyzes the EMG information from the sensor system 410 and determines the intended gesture based on the received EMG information. The EMG control module 420 produces gesture instructions to the VR control module 430. The VR control module 430 receives the gesture instructions and causes the VR display 440 to display a virtual representation of the intended gesture. The actuator 406 may be used to provide information to the VR control module 430, such as on/off information or general actuation information.

The VR control module 430 and the VR display 440 may be part of a VR system 450. One such system is the VR system described in U.S. Patent App. No. 2016/0162012 Al to Chang et al, titled Virtual Reality System and Method for Controlling Operation Modes of Virtual Reality System, published Jun. 9, 2016 (hereinafter, "Chang"), which is incorporated by reference. The sensor system 410, EMG control module 420, and VR control module 430 may each be integrated into its own separate hardware, or one or more of them may be integrated into the same hardware. The VR system 450 may comprise a detector 435 which, in coordination with the kinematic sensor 407, allows the VR system 450 to detect the kinematics of a portion of the user—for instance, detecting the position of the user's residual limb. The detector 435 may be, in one embodiment, a base station of the kind described in Chang. In related or alternative embodiments, other forms of virtual reality tracking may be employed, such as inside-out tracking, markerless inside-out tracking, positional tracking, outside-in tracking, or other virtual reality tracking methodologies known in the art.

Using the interface 400, a user may flex her muscles in a manner that indicates she wishes to perform a gesture, such as wrist rotation. The sensor system 410 receives EMG information from the user and transmits it to the EMG control module 420. The EMG control module 420 determines that the user intends to perform the wrist rotation gesture. The EMG control module 420 then sends a gesture instruction to the VR control module 430 that instructs the VR control module 430 to generate instructions to rotate a virtual reality wrist displayed on the VR display 440. The VR display 440 then displays the rotation of the virtual reality wrist, which the user can view. It should be understood that the user may be an amputee, and so even though she is capable of flexing her muscles in a manner indicating a wrist rotation gesture, she does not have a physical wrist. Using the VR display 440 to watch the rotation of the virtual reality wrist can give the user a sensation of having an artificial wrist, even though no artificial wrist is connected to her residual limb. The same is true for other limb gestures, such as wrist flexion, wrist pronation, hand open, no motion, hand closed, wrist supination, wrist extension, wrist abduction, and wrist adduction.

"Myoelectric control" refers to the control of an actual device or a virtual reality device (such as the virtual reality wrist described above) using EMG information. Various algorithms may be used to perform myoelectric control. A myoelectric control module may be programmed into an EMG control module 420. One form of myoelectric control can be termed "direct control". Direct control measures the EMG information over a control site and uses basic signal processing to extract an amplitude feature from the signal, for instance, the mean absolute value (MAV) or root mean square (RMS) value of the signal. The value of the amplitude feature may then be compared to a preset threshold to determine if the user intends to make a motion.

An extension of this type of control, termed 'direct proportional control', uses the value of the amplitude feature to control the speed of actuation of the prosthesis, as it is well known that the amplitude features are proportional to intensity of a muscular contraction. Both direct control and direct proportional control strategies are intuitive provided that physiologically appropriate control sites are available from which to measure the EMG.

The intuitiveness and number of motion classes of the system is limited by the number of physiologically appropriate control sites available. "Amplitude multi-state" myoelectric control is closely related to direct control described above; however, in this case the dynamic range of the amplitude feature is divided into discrete threshold levels. Each of the threshold levels is mapped to an appropriate motion class of the prosthesis. In real-time operation, the extracted amplitude feature is compared to the threshold levels, and the appropriate motion class is actuated.

A three-state controller is another amplitude multistate controller. Although it is possible to partition the amplitude range to more than three states, it becomes difficult for the user to control due to the increased cognitive load and the randomness associated with the EMG. The benefits of using multi-state controllers are that more motion classes can be controlled given a limited number of control sites; however, the motion classes may no longer be mapped to physiologically appropriate control sites.

Instead of comparing the amplitude feature to a predetermined threshold, the rate of change of the amplitude could also be used for myoelectric control. In this type of control, slowly changing amplitudes corresponding to one motion class while quickly changing amplitudes corresponds to another. This is sometimes called fast-slow or slow-fast control. After the motion is activated, proportional control is achieved through mapping the actual value of the amplitude feature to the speed of the device. Thus, three-state proportional control can be achieved using this type of rate-sensitive controller. The limitations of this device are similar to the previously mentioned multi-state controllers; the motion classes may not be mapped to physiologically appropriate control sites.

Mode switching is another aspect of conventional control. Conventional control systems have historically been limited to a single Degree of Freedom ("DOF"); however, a mode switch may be used to add an additional DOF. An example of conventional control with a mode switch would be a dual site direct control system for a transhumeral amputee. The biceps and triceps muscles may be used to activate elbow flexion and elbow extension respectively. A co-contraction may be used to switch to a hand DOF, after which biceps and triceps muscles would be used to activate hand close and open. The number of co-contractions and the length of time the person must co-contract can be varied to form a Morse-code like pulsing system. Each pulse sequence then corresponds to a different gesture to control, or hand-grasp pattern to activate. Mechanical switches may be used instead of motion co-contractions to switch between DOFs, and gestures measured through an inertial measurement unit can also be used as a mode-switch.

Information extracted from patterns contained in the myoelectric signal can also be used for control purposes. In an embodiment, the EMG control module 420 may be defined as a pattern recognition classifier. Pattern recognition classifiers include but are not limited to modules which use for control one or more of the following algorithms: classification algorithms, clustering algorithms, ensemble learning algorithms, general algorithms for predicting arbitrarily-structured sets of labels, multilinear subspace learning algorithms, real-valued sequence labeling algorithms, regression algorithms, and sequence labeling algorithms.

Classification algorithms or supervised algorithms predicting categorical labels include both parametric and non-parametric algorithms among others. Parametric classification algorithms include but are not limited to linear discriminant analysis, quadratic discriminant analysis, and a maximum entropy classifier, also known as logistic regression or multinomial logistic regression. Nonparametric classification algorithms include but are not limited to decision trees and/or lists, kernel estimation, K-nearest-neighbor algorithms, Naive Bayes classifier, neural networks (multilayer perceptrons), perceptrons, support vector machines, and gene expression programming. Clustering algorithms or unsupervised algorithms predicting categorical labels include but are not limited to categorical mixture models, deep learning models, hierarchical clustering (agglomerative and/or divisive), K-means clustering, correlation clustering, and Kernal principal component analysis ("Kemal PCA"). Ensemble learning algorithms or supervised meta-algorithms for combining multiple learning algorithms together include but are not limited to boosting (meta-algorithm), bootstrap aggregating (bagging), ensemble averaging, mixture of experts/hierarchical mixture of experts, and random forest. General algorithms for predicting arbitrarily-structured sets of labels include but are not limited to Bayesian networks and Markov random fields. Multilinear subspace learning algorithms—one of the uses of which is to predict labels of multidimensional data using tensor representations—can be categorized in one way as unsupervised and include among others, multilinear principal component analysis (MPCA). Real-valued sequence labeling algorithms—one use of which predicts sequences of real-valued labels—can be categorized in one way as supervised and include, among others, Kalman filters and particle filters. Regression algorithms, which can be used to predict real-valued labels, can be categorized as either supervised or unsupervised. Supervised regression algorithms include but are not limited to Gaussian process regression (kriging), linear regression and extensions, and neural networks and deep learning methods. Unsupervised regression algorithms include, but are not limited to, independent component analysis (ICA) and principal components analysis (PCA). Sequence labeling algorithms which can be used to predict sequences of categorical labels, also include supervised and unsupervised categories. Supervised sequence labeling algorithms include, among others, conditional random fields (CRFs), hidden Markov models (HMMs), maximum entropy Markov models (MEMMs), and recurrent neural networks. Unsupervised sequence labeling algorithms include, but are not limited to, hidden Markov models (HMMs).

Pattern recognition control operates on the assumption that at a given electrode location, the set of features describing the myoelectric signal will be repeatable for a given state of muscle activation and will be different from one state of activation to another. In pattern recognition control, the EMG signals may be represented using features, which are statistical descriptions of the signal. Non-inclusive but commonly used examples of features include the amplitude of the signal, the variance of the signal, the number of time the signal crosses zero, the short-time Fourier transform coefficients, wavelet coefficients, auto-regressive coefficients, and the Willison amplitude. These features across all movements may then be learned using machine learning techniques. Examples of commonly used learning algorithms include expectation maximum, gradient descent with back-propagation, or linear/non-linear regression. After the model has been learned, EMG signals are classified in real-time using the mathematical model. Examples of commonly used models include artificial neural networks, linear discriminant analysis, support-vector machines, quadratic discriminant analysis and Gaussian-Mixture models.

Regardless of what type of myoelectric control is used, the objective is to determine what gesture the user is intending to perform. In an embodiment, the EMG control module 420 can perform one or more of the previously listed algorithms, and alternatively can be programmed with new algorithms as they become available.

In an embodiment, ten features of time domain and auto-regression are extracted from the EMG information received by sensors 405. The time domain features include mean relative value; waveform vertical length; zero crossing; and slope change. The remaining features are auto-regression features. In an embodiment using a six-channel EMG sensor system and 200 ms windows of EMG data, the raw EMG data per window will be contained in a matrix of six columns by 200 rows, or 1200 elements in size. Each feature will be calculated for each EMG channel (ten features*six channels=60), so the 6×200 matrix is reduced to a 60×1 vector. This vector is then provided as an input to the EMG control module 420 when defined as a pattern recognition classifier.

Still with respect to FIG. 7, when the EMG control module 420 is defined as a pattern recognition classifier, the EMG control module 420 may require pattern recognition training in order to accurately determine the user's intended gesture.

Figure 12:
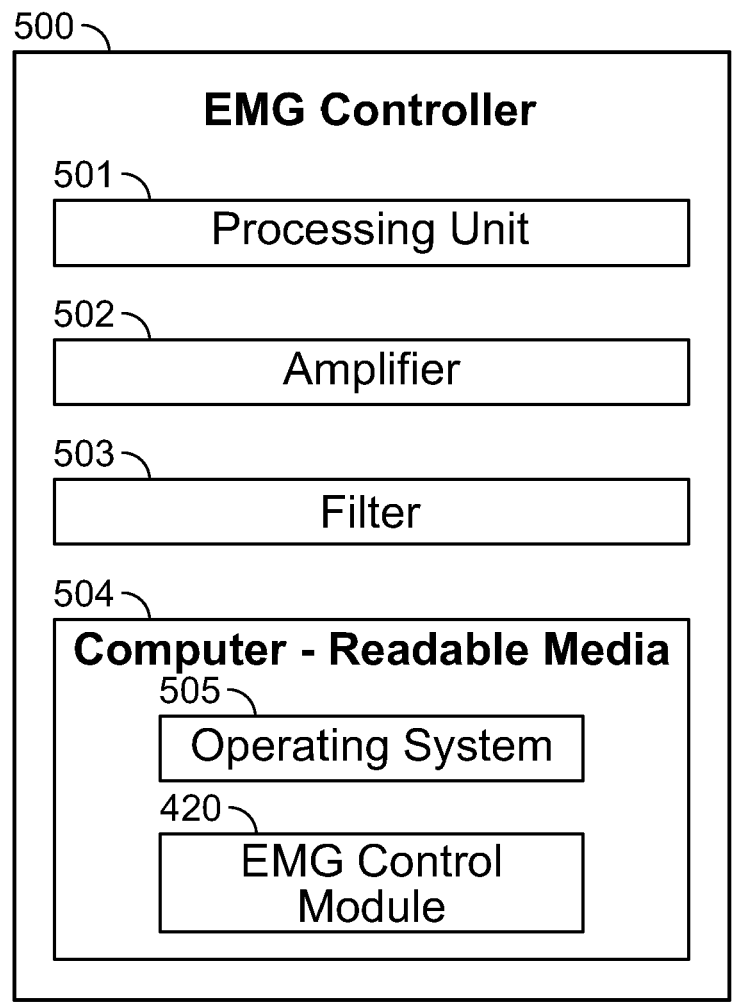
FIG. 12 is a block diagram of an exemplary EMG controller.

As shown in FIG. 12, the EMG control module 420 may be provided on computer-readable media 504, such as memory. The computer-readable media 504 may also comprise an operating system 505 for operation of an EMG controller 500. The EMG controller 500 may comprise one or more processing units 501 for processing the EMG control module 420, as well as an amplifier 502 and a filter 503 for amplifying and filtering EMG signals from sensors 405.

Figure 8:
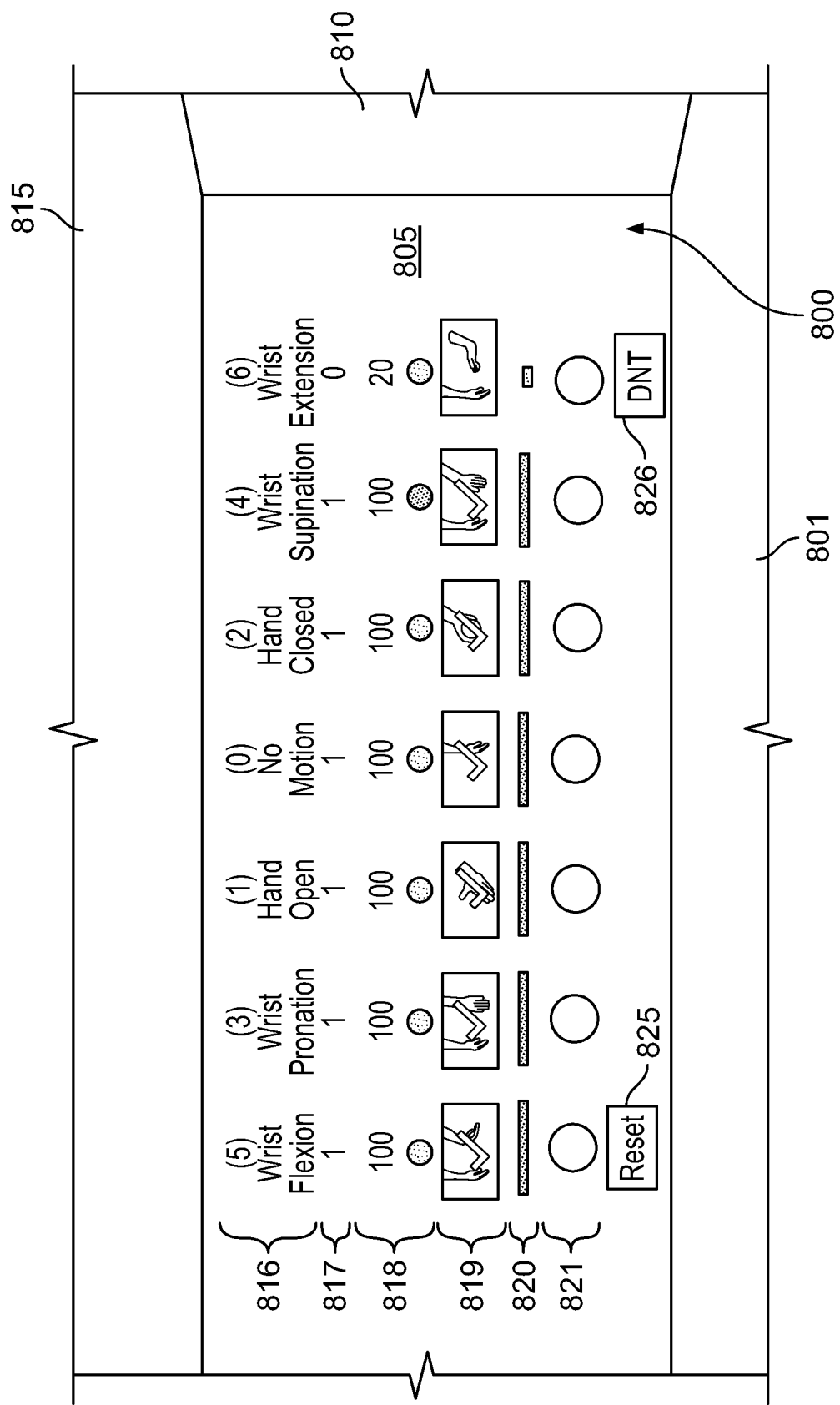
FIG. 8 is a view of an exemplary virtual reality display corresponding to static training.
Figure 9:
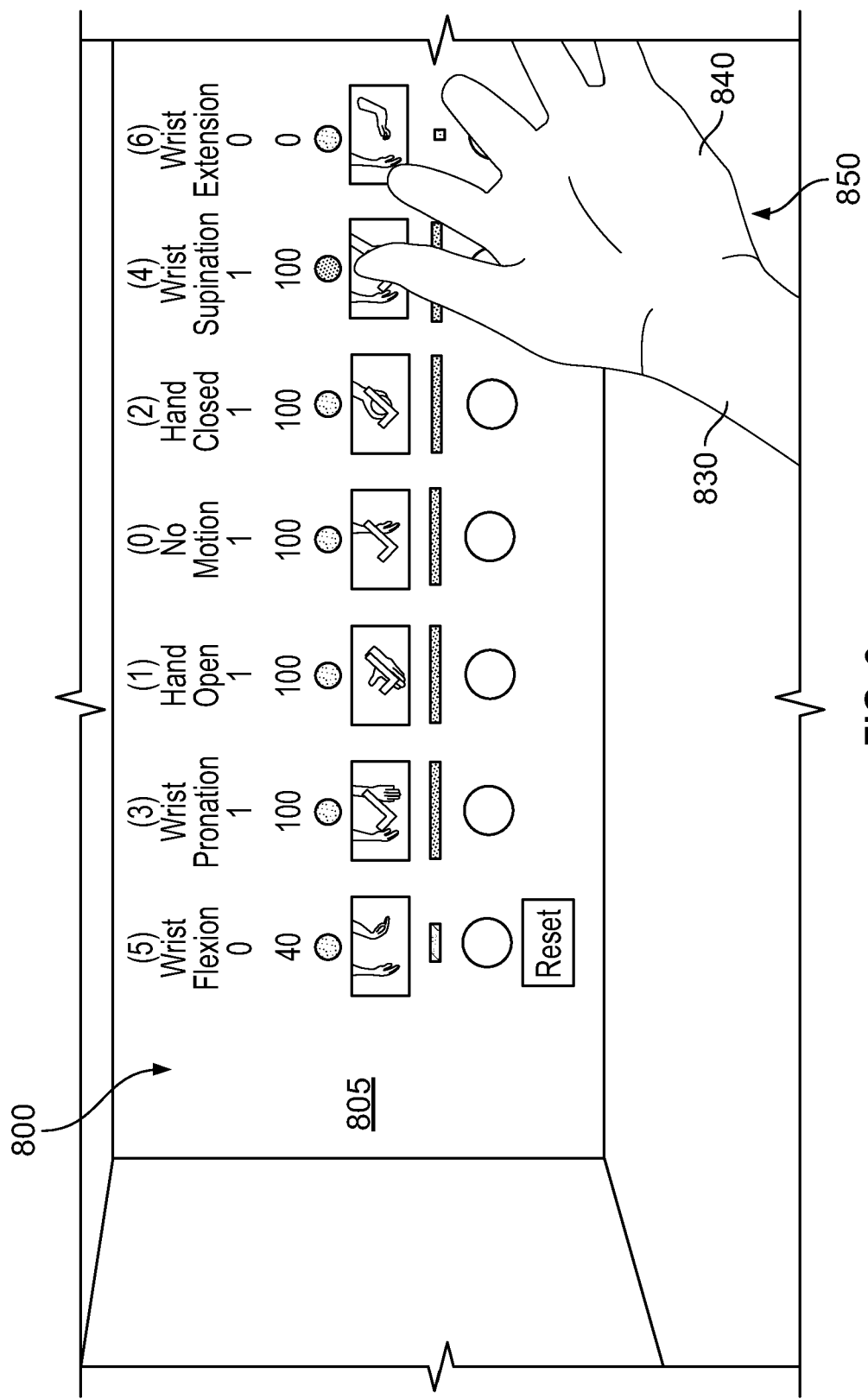
FIG. 9 is another view of the exemplary virtual reality display in FIG. 8.

In an embodiment, the EMG control module 420 may be trained using aspects of the VR system 450. FIGS. 8-9 show images that may be displayed on the VR display 440 during training of the EMG control module 420. FIG. 8 shows a three-dimensional VR space 800 comprising a back wall 805, a side wall 810, and a ceiling 815. Positioned on the back wall 805 are shown a series of interactive columns, with each column representing information about a particular gesture to be trained. The top of each column at 816 identifies the name of the gesture to be trained (wrist flexion, wrist pronation, hand open, no motion, hand closed, wrist supination, and wrist extension). Below each name at 817 is a number that identifies the number of times the respective gesture has been trained. Next is a number and an image at 818 that indicates the portion of the most recent training session that has been completed. The image may have a color, such as green, when the EMG control module 420 is being trained with the respective gesture. Next at 819 is an image of the gesture the user is intended to perform, which may be superimposed by a check mark if the training has been complete. For instance, the image to the farthest left in 819 shows the "wrist flexion" gesture, displaying a hand in a no motion position and a hand in a wrist flexion position. This helps the user visualize the intended gesture to make. At 821 an start/stop button is displayed which allows the user to activate a training session for a respective gesture. For instance, the button to the farthest left in 821 may be selected in order to start a training session for the wrist flexion gesture and to stop an ongoing training session for the wrist flexion gesture.

FIG. 9 shows a representation of the VR space 800 which further includes a virtual limb 850 comprising a forearm 830 and a hand 840. In order to select a button in 821, the user moves her real-life limb. The sensor system 410 detects the movement of the user's real-life limb and sends corresponding information to the VR system 450 to cause a corresponding gesture of the virtual limb 850. In this way, the motion of the virtual limb 850 can be positioned to point to one of the start/stop buttons in 821. A trace line, such as a dashed line, may extend from the tips of the fingers of the hand 840 towards the back wall 805. When the virtual limb 850 is positioned so that the tips of the fingers of hand 840 are pointed at a start/stop button in 821, the trace line may change color (such as from red to green) and the start/stop button in 821 may also change color (such as from red to green). At that time, the user or clinician may initiate a training phase for the respective gesture, such as by actuating the actuator 406.

The EMG control module 420 begins to train based on the EMG information provided by the sensor system 410. In an embodiment, the EMG control module 420 is defined as a linear discriminant analysis (LDA) pattern recognition classifier. In this embodiment, the control module 420 is arranged with gesture classes 421. Each class in gesture class 421 may be correlated with exactly one degree of freedom movement. In an embodiment, the gesture classes 421 comprise one class for each of wrist flexion, wrist pronation, hand open, no motion, hand closed, wrist supination, wrist extension, wrist abduction, and wrist adduction.

For example, when the start/stop button in 821 associated with the no motion gesture is actuated, the user is instructed to hold her residual limb in a fixed position without exerting any muscles that would indicate one of the other gestures. The sensor system 410 detects the EMG signals from the user's forearm and sends EMG information to the EMG control module 420, which now is in a training state. The EMG control module 420 associates the incoming EMG information with a "no motion" class for the duration of the "no motion" training. The "no motion" training period may be for a specified duration, such as 2-3 seconds or another appropriate time. During the "no motion" training period, the position of the forearm will move if the user moves her residual limb. Likewise, during a training period, the position and orientation of the hand 840 will move as the user actuates her muscles in a manner intended to move the hand 840 to match the respective gesture 816.

At the completion of the "no motion" training, the EMG control module 420 completes the training state. The user is then able to select another gesture category to train on, or to re-train the "no motion" category again. In each training session, the EMG control module 420 enters a training state in which the EMG control module 420 is trained to the gesture category selected by the user. In this way, the user may train each class in gesture classes 421 with EMG information that corresponds to the user's movements conducted during a training session. Feature extraction and classification may be performed in real-time, which can allow the user to test the classifier's performance following each collected set of training data.

Still with respect to FIG. 8, buttons reset 825 and DNT 826 are shown positioned on the back wall 805. Reset 825 resets the training data stored in the EMG control module 420 and the gesture classes 421, so that the EMG control module reverts to an untrained state. DNT 826 allows the interface 400 to collect EMG information collected by the sensor system 410 but not include that information in training data. One purpose of the DNT feature (which stands for "do not train") is so that the collected data can be used in offline analysis to determine overall algorithm efficiency and to determine classifier effectiveness.

In an embodiment, the hand 840 may start a training session in a semi-closed position, so it has room to open or close. The speed of the movement of hand 840 may depend on information provided by kinematic sensors 407. For instance, the kinematic sensors 407 may provide a proportional control value to regulate the speed of movement of the hand 840. In an embodiment, the kinematic sensors 407 provide a value between 0 and 1 to the VR control module 430 which reflects the speed of intended hand movement. If the value is closer to 0, the hand movement is correspondingly slow. If the value is closer to 1, the hand movement is correspondingly fast. In another embodiment, the speed of the movement of the hand 840 may depend on a measurement of the EMG signal provided by the user. For instance, a strong EMG signal may result in a proportional control value that makes the hand move quickly and a weak EMG signal may result in a proportional control value that makes the hand move slowly. Hand and wrist gestures may be independent. For instance, if the hand is set in a "hand closed" position, and wrist flexion is then trained, the VR display 440 will display the wrist flexing while the hand remains in a hand closed position.

The EMG control module 420 may provide a vector of size n to the VR control module 430, where n is equal to the number of classes in gesture classes 421. Each value in the vector may be +1, 0, or −1. +1 in position i reflects a movement in one direction for class i. For instance, if the vector has a value of +1 at position 5, which may be the hand open/close gesture position, this can instruct the VR control module to close the hand 840. If the vector has a value of −1 at position 5, which may be the hand open/close gesture position, this can instruct the VR control module to open the hand 840. As another example, if the vector has a value of −1 at position 6, which may be the wrist flexion/extension gesture position, this can instruct the VR control module to flex the wrist 830. If the vector has a value of +1 at position 6, which may be the wrist flexion/extension gesture position, this can instruct the VR control module to extend the wrist 830.

There are various ways to instruct a user to position her residual limb during training. In an embodiment, the type of training described above with reference to FIGS. 8-9 is conducted while the user keeps her residual limb in a fixed position, while during the different training phases actuates different muscles intended to reflect desired hand or wrist gestures. For instance, the user may keep her arm in a single orientation, with the residual limb parallel to the floor and the elbow at a 90° angle, while collecting training data on each of the movements. The user's upper-arm may remain parallel and against her body and remain still during the training period. This type of training may be referred to as "static training."

Static training may be supplemented by, or in some embodiments replaced with, training in which the user moves her residual limb in real-life in three dimensions—in front of/behind her; to her left/right; and above/below her. In this type of training exercise, referred to as "dynamic training," a user may move her residual limb, unconstrained, around her body while performing each gesture in the gesture class 421. A user can be encouraged to extend/flex her elbow or move her residual limb into a variety of orientations, such as pointing the residual limb upwards towards the real-life ceiling or downwards towards the real-life floor.

Figure 10:
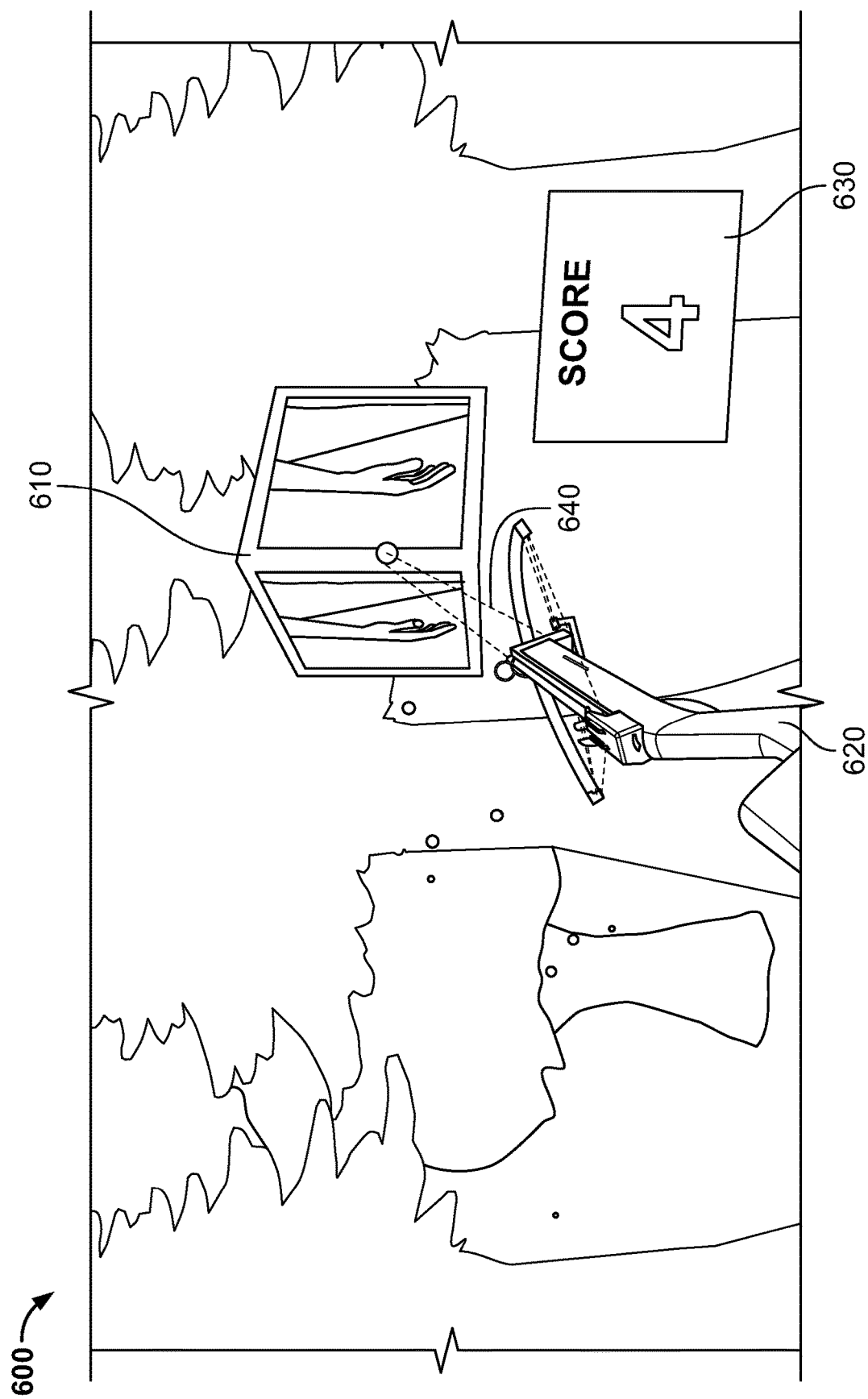
FIG. 10 is a view of an exemplary virtual reality display corresponding to dynamic training.
Figure 13:
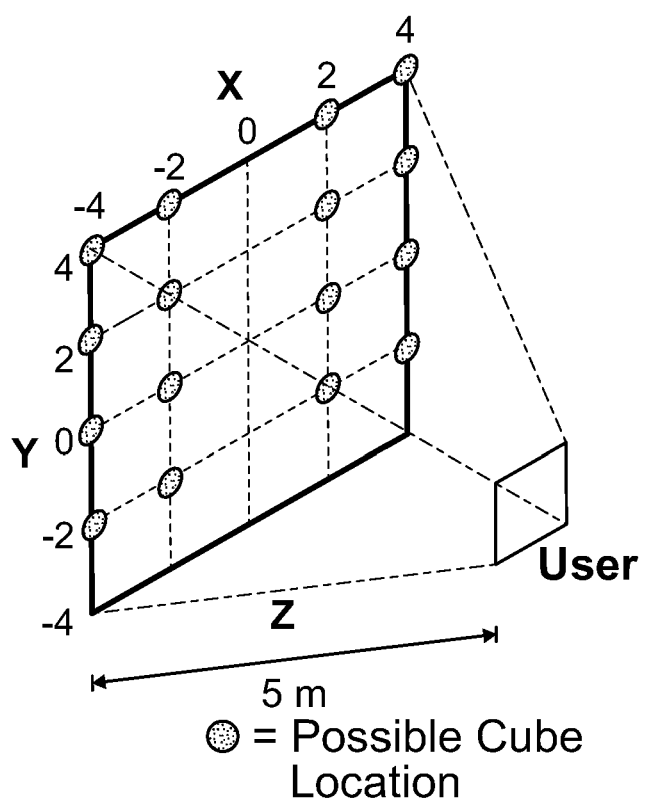
FIG. 13 is a representation of exemplary positions of targets in a virtual environment.

One exemplary method for conducting dynamic training is referred to herein as "target achievement control," in which the user moves her residual limb to cause a virtual limb to point to a virtual target in a virtual three-dimensional space. FIG. 10 shows an image of a virtual target 610 in a virtual three-dimensional space 600 displayed on a VR display 440. The virtual limb 850 shown in FIGS. 8-9 may be replaced with a "limb avatar," which is a virtual representation of the user's real-life limb. As shown in FIG. 10, the limb avatar takes the form of a crossbow 620. As the user moves her muscles, the interface 400 detects the movement as described above and causes the crossbow 620 to make a corresponding movement 640 within the space 600. The user may stand facing a single direction, or stand but move her head to look around the space 600, in order to look for a virtual target 610. The virtual target 610 may pseudo-randomly appear in one of a plurality of discrete positions at a time. As shown in FIG. 13, from the user's perspective, a virtual target 610 could appear, for example, in one of four horizontal positions (two on either side), and four vertical positions, with some appearing above the user and some appearing below. In target achievement control training, once the user has pointed the crossbow 620 to a virtual target, such as target 610, the user contracts her muscles in a manner to reflect an intended gesture.

To give a non-limiting example, the user may contract her muscles in a manner to reflect an intended gesture shown on the virtual target 610, such as a "hand close" gesture. The sensor system 410 detects the EMG signals from the user's forearm and sends EMG information to the EMG control module 420, which again is in a training state. The EMG control module 420 associates the incoming EMG information with a "hand close" class for as long as the user is shooting the virtual target 610. Once the user has stopped shooting the virtual target 610, the EMG control module 420 completes the training state. The user is then able to select another target to shoot, which is associated with the same or a different gesture. The process is repeated as needed to train EMG control module 420. In each shooting session, the EMG control module 420 enters a training state in which the EMG control module 420 is trained to the gesture category associated with the virtual target. In this way, the user may train each class in gesture classes 421 with EMG information that corresponds to the user's movements conducted during a training session specific to the associated gesture category. One feature of this type of dynamic training is that each gesture class in the gesture classes 421 may be trained with EMG information generated while the user's residual limb is at different orientations. With reference again to FIG. 13, the user must reach her residual limb upward to target a virtual target above her head, and must lower her residual limb downward to target a virtual target below her head. Raising and lowering the residual limb activates different muscles at different intensities, which changes the nature of the EMG signals produced by the user's muscles. However, training data remains categorized within each gesture class. As a result, training data from the user making a "hand close" gesture at a low target, training data from the user making a "hand close" gesture at a mid-level target, and training data from the user making a "hand close" gesture at a high target are all used to train the same "hand close" class in the gesture classes 421. Although the prior description is with reference to the "hand close" gesture, the description above equally applies to the other gesture classes available in the system.

The virtual target 610 may take many visual forms. For instance, restricting the user from seeing the associated gesture of the virtual target 610 until the crossbow 620 points at the virtual target 610 may help the user from pre-emptively shooting before the crossbow 620 is in the proper position. Furthermore, the user can be encouraged to avoid firing arrows from the crossbow 620 when moving between cubes, to assist in improving control. Fired arrows may be colored with a color that represents the gesture being performed (such as blue for "hand closed", orange for "hand open", and the like). When the user was not pointing the crossbow 620 at a virtual target 610, a non-gesture image (like the image of a stop sign) may be shown. Once the user pointed the crossbow 620 at the virtual target 610, the gesture associated with the virtual target may be shown on an outer surface of the virtual target 610 or in proximity to the virtual target 610, or otherwise displayed on the VR display 440. Alternately the associated gesture may be announced audibly to the user. Once the crossbow 620 is pointed at the virtual target 610, the user may perform the associated gesture. The EMG control module 430 may determine whether the user has successfully performed the associated gesture, and send a gesture instruction to the VR control module 430 indicating whether or not the user has successfully performed the associated gesture. If the user has successfully performed the associated gesture, this may cause the virtual target 610 to transform. In an embodiment, the virtual target 610 may grow in size until it "breaks" visually. In an embodiment, each arrow fired represents one window of EMG data, therefore, arrows are fired every 25 ms, for example, and the threshold to break a virtual target 610 may be set to 100 arrows for example. A virtual target 610 may be designed so that it increases in size only if the correct arrow color (which reflects the correct estimated gesture from the user's EMG information) matches the gesture associated with the virtual target 610. However, incorrect estimated gesture information may still be used in adaptation. This can be used as feedback to the user, so she is aware of her progress over time.

In another embodiment, the virtual target 610 may disappear at a set time, starting from the first time the crossbow 620 is pointed to it. For instance, the virtual target 610 may disappear after three seconds after the crossbow is pointed to it. If the user "fires" all the correct arrows from the moment she points at the virtual target 610, it would take 2.5 seconds (25 ms windows*100 arrows) to break the virtual target 610, indicating a success. A success sound may be presented to the user once the virtual target 610 breaks. If the user is unable to destroy the virtual target 610 within the time limit, the virtual target 610 may disappear, and the next virtual target can appear at another location. A different sound may be presented to the user to indicate a failed attempt at breaking the virtual target 610. This again may be used as feedback for the user.

The EMG control module 420 can be programmed to send gesture instructions to the VR control module 430. Each output movement can be mapped to a button on a commercially available VR controller, such as controller 120. The outputs can be sent over a wired connection to the controller 120. For example, rather than pressing a button on a controller in order to accelerate a vehicle in a video game as an able-bodied individual would do while playing a game, an amputee can contract a muscle which mimics that button press to perform the same action. The EMG control module 420 can also communicate directly to the control module 430 using a wireless link. For example, a TCP/IP connection can be established to the VR system 450. In this situation, the VR system 450 may comprise wireless means known in the art. Gesture instructions from the EMG control module 420 can be programmed to emulate controls from a directional pad (DPAD) game controller and button clicks from controller buttons. Thus any virtual reality game that uses a controller with an actuator can be emulated.

As described earlier, EMG signals can be detected from an amputee's residual limb and are converted into video game control signals by the EMG control module 420. The EMG control module 420 can perform various clinically available EMG control paradigms. The VR system 450 can utilize therapist-defined rehabilitation protocols to customize the game controls and environment. The VR system 450 can collect and report patient performance metrics back to the clinician, which can help the clinician progress and optimize protocols to achieve the patient's functional rehabilitative goals. For example, a clinician may create an initial gameplay profile that may rely on mastery of a limited or specified set of contractions made by the user. Once a certain level of mastery of these clinician-defined metrics is achieved, the gameplay may progress to require the user to make additional contractions, until the required level of neuromuscular control is achieved. Monitoring of a user's performance as well as the adjustment of rehabilitation protocols used for gameplay may be done in real time either on site, or remotely via an internet connection. Such a design lends itself to ongoing telemedical interactions to allow protocol progression and allows for adaptation of the system as the patient's abilities change or she upgrades her assistive device or associated components.

In another embodiment, a user must target and shoot falling balloons of different colors. The user moves the orientation and position of her residual limb to change where the limb avatar is pointed. When she has positioned the limb avatar appropriately, she can make a muscle contraction to shoot a bullet or laser-beam to burst the balloon. The different colors of the balloons correspond to different muscle contractions that would be used as part of the myoelectric control interface, and changes in size are based on performing the correct action. Colors and the corresponding actions are shown at the bottom of the screen so the user can learn which color corresponds with which action. As a balloon falls, the user must recognize the color of the balloon and match a specific movement to shoot the balloon and gain points (if the balloon hits the ground no points are awarded). When a contraction is made, the color of the bullets will also correspond to the muscle contraction. For example, when a user sees a green balloon, green bullets will appear if the person performs the correct gesture with her residual limb. The user may shoot a target balloon multiple times to make it expand, until it bursts, if she has performed the correct action. A user's score can increase in inverse proportion to the time taken to explode the balloon. The user's score (example shown by score 630 in FIG. 10 can) increase or decrease depending on the size and position of the balloon. If a user performs the incorrect movement and a different color bullet (representing a different gesture) hits the balloon, their score may decrease. The score may be saved locally or uploaded to a central server.

A user can progress to a different level by changing the speed or size at which targets appear in the game play environment. When using a VR control system 450, the virtual targets can be placed in different areas of the game space so that the user has to move to a different position and place their limb in a different orientation and position to successfully burst the target. Weights can also be added to the sensor system 410 or to the user's arm, to simulate the weight of a prosthetic device. Weights may be added incrementally as the individual progresses through her rehabilitation protocol. The application of weights may be used with any game played in the VR system 450. In another embodiment, to promote bimanual activities, a cross-hair target can be controlled using the user's sound limb. When a user has placed the target properly, they can use their affected limb to shoot at the target.

In another game, a user holds a simulated pump-action shotgun using the VR controller. The user's relative orientation between the two controllers, which are either being held or attached to the user, may be used to aim the shotgun, and the relative motion between the two controllers may be used to initiate the pump-action gun to reload. The user then can make an muscle contraction to pull the trigger to shoot the gun. Targets can appear anywhere in the game to encourage the user to move positions and limb orientations.

Figure 11:
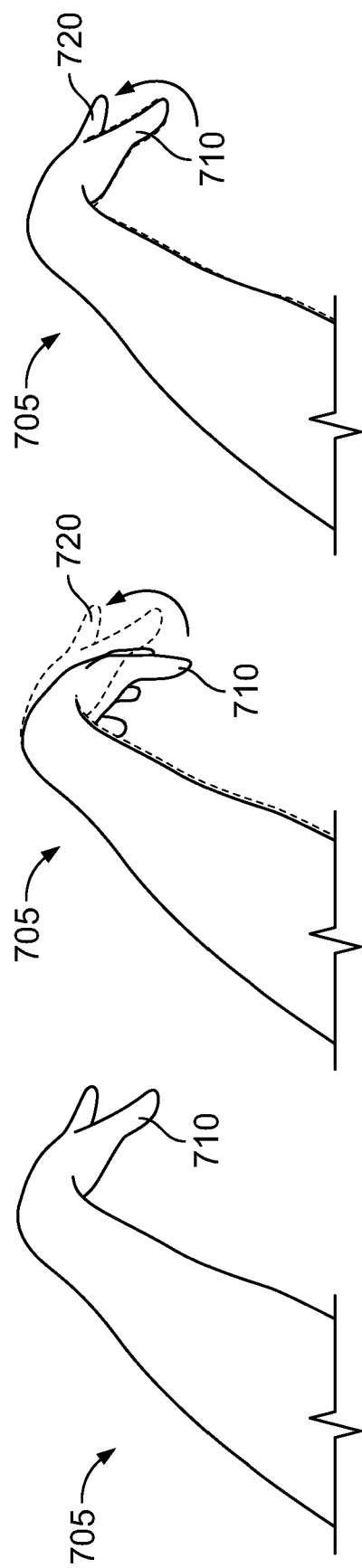
FIG. 11A is a virtual reality representation of an exemplary limb avatar.
FIG. 11B is a virtual reality representation of the exemplary limb avatar shown in FIG. 11A, partially superimposed over an exemplary target position.
FIG. 11C is a virtual reality representation of the exemplary limb avatar shown in FIG. 11A fully superimposed over the exemplary target position of FIG. 11B.

After the EMG control module 420 has been trained, the VR system 450 can create a virtual environment in which the user attempts to make specified gestures of a virtual limb. FIGS. 11A-C show an example of such a virtual environment. FIG. 11A displays a limb avatar 710 in a virtual space 705. The limb avatar 710 moves its forearm, wrist, and fingers in response to EMG information and optionally in response to kinematic information. FIG. 11B additionally displays a target position 720. The goal of the game displayed in FIGS. 11A-C is for the user to move her muscles in such a way as to cause the limb avatar 710 to match the same position as the target position 720. If the user successfully matches the limb avatar 710 to the position of the target position, shown in FIG. 11C, the VR system 750 may provide positive feedback to the user. For instance, the color of the outer surface of the limb avatar 710 may change; a positive feedback sound may be played; or other positive feedback may be provided.

In an embodiment, the virtual environment shown on VR display 440 may comprise an instruction mechanism, such as a virtual coach, that instructs the user in making appropriate movements of her residual limb. For instance, the instructions can guide the user to slow down if she is moving her residual arm too quickly during dynamic training. Likewise, when a user performs dynamic training, a user tends to rotate their limb while making a hand open or hand close movement. The instructions would detect that the user is rotating her limb and provide an instruction to the user to stop rotation. In another example, a user may make muscle contractions that are too strong or too loose. The instructions can instruct the user in the proper contraction strength, and have the user perform a range of contraction strengths. The instructions could be given in words or pictures displayed on the VR display 440, could be provided audibly or with haptic feedback to the user, or could be given by an avatar "virtual coach" displayed on the VR display 440.

In other embodiments, the interface 400 could be revised so that the VR system 450 is replaced with a two-dimensional visual display, such as a computer display. Examples of computers could include desktop computers, laptop computers, smartphones, tablets, and the like. The VR control module 430 could be replaced with a two-dimensional control module programmed to convert gesture instructions from the EMG control module 420 into control commands for programs operating on a computer display, such as Tetris or Pac-Man.

Once the EMG control module 420 has been trained, it may be arranged for use with a real-life assistive device 460. The assistive device 460 may be a myoelectric device, such as a myoelectric prosthetic arm. One aspect of using a trained EMG control module 420 to operate the assistive device 460 is that the EMG control module 420 is trained to identify the gestures the user wishes to make. The EMG control module 420 can provide a gesture instruction to the assistive device 460, and the assistive device 460 will make the intended gesture. Examples of myoelectric assistive devices may include, but are not limited to the U3+ Arm from Motion Control, Inc. (Salt Lake City, UT), the bebionic hand from Otto Bock (Austin, TX), or the assistive device described in U.S. Patent Publication No. 2015/0216681 AI, Modular and Lightweight Myoelectric Prosthesis Components and Related Methods (published Aug. 6, 2015), which is incorporated herein by reference.

The virtual reality environment displayed by VR display 440 may be generated using the Unity virtual reality platform by Unity Technologies (San Francisco, CA). The virtual reality limbs may be generated by software for modelling 3-dimensional humanoid characters, such as MakeHuman by the MakeHuman Team (www.makehuman.org). The limb model may be comprised as a plurality of joint representations. The wrist representation may have three degrees of freedom (for wrist rotation, wrist flexion/extension, and wrist adduction/abduction) and each finger joint representation may have a single degree of freedom (for opening or closing the hand).

The embodiments described herein provide several advantages for individuals who use myoelectric arm prostheses or other assistive devices. Such advantages, in addition to those already described, include: work toward more accurate programming of the assistive device specified for particular users to encourage more efficient and effective transition to an assistive device; facilitating motor practice and improvements in assistive device control independently of the user's assistive device brand or type; having monitoring and diagnostic capabilities to optimize treatment strategies and sequence of progression throughout the rehabilitation process; simulating the weight and inertia of an assistive device; promoting training during bimanual activities; promoting work within the myoelectric workspace; able to be used by the user at her home following an initial tuning session at a clinic.

Although the techniques have been described in language specific to structural features and/or methodological acts, it is to be understood that the appended claims are not necessarily limited to the features or acts described. Rather, the features and acts are described as example implementations of such techniques. Female pronoun references to users of the system should be understood to apply to both male and female users of the system.

The operations of the example processes are illustrated in individual blocks and summarized with reference to those blocks. The processes are illustrated as logical flows of blocks, each block of which can represent one or more operations that can be implemented in hardware, software, or a combination thereof In the context of software, the operations represent computer-executable instructions stored on one or more computer-readable media that, when executed by one or more processors, enable the one or more processors to perform the recited operations. Generally, computer-executable instructions include routines, programs, objects, modules, components, data structures, and the like that perform particular functions or implement particular abstract data types. The order in which the operations are described is not intended to be construed as a limitation, and any number of the described operations can be executed in any order, combined in any order, subdivided into multiple sub-operations, and/or executed in parallel to implement the described processes. The described processes can be performed by resources associated with one or more device(s) such as one or more internal or external CPUs or GPUs, and/or one or more pieces of hardware logic such as FPGAs, DSPs, or other types of accelerators.

All of the methods and processes described above may be embodied in, and fully automated via, software code modules executed by one or more general purpose computers or processors. The code modules may be stored in any type of computer-readable storage medium or other computer storage device. Some or all of the methods may alternatively be embodied in specialized computer hardware.

Conditional language such as, among others, "can," "could," "might" or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples or that one or more examples necessarily include logic for deciding, with or without user input or prompting, whether certain features, elements and/or steps are included or are to be performed in any particular example. Conjunctive language such as the phrase "at least one of X, Y or Z," unless specifically stated otherwise, is to be understood to present that an item, term, etc. may be either X, Y, or Z, or a combination thereof.

Any routine descriptions, elements or blocks in the flow diagrams described herein and/or depicted in the attached figures should be understood as potentially representing modules, segments, or streams of code that include one or more executable instructions for implementing specific logical functions or elements in the routine. Alternate implementations are included within the scope of the examples described herein in which elements or functions may be deleted, or executed out of order from that shown or discussed, including substantially synchronously or in reverse order, depending on the functionality involved as would be understood by those skilled in the art. It should be emphasized that many variations and modifications may be made to the above-described examples, the elements of which are to be understood as being among other acceptable examples. All such modifications and variations are intended to be included herein within the scope of this disclosure and protected by the following claims.

What is claimed is:

1. An apparatus for prosthetic training, comprising:
an arm band for training a control module associated with a prosthetic limb including:
a plurality of housing elements defining a housing,
one or more electromyography (EMG) sensors provided in at least one of the plurality of housing elements, and
one or more kinematic sensors;
one or more processing units in operable communication with the one or more EMG sensors of the arm band and the control module of the prosthetic limb, the one or more processing units configured to:
receive EMG data of a residual limb from the one or more EMG sensors, predict an intended gesture of a user wearing the arm band from the EMG data, and generate a gesture instruction in response to a user performing a training gesture; and
a virtual reality (VR) system configured for training the control module of the prosthetic limb using the arm band, comprising:
a visual display,
one or more detectors for motion tracking, configured to:
receive data from the one or more kinematic sensors to determine a position or orientation of the arm band relative to the VR system, and
a VR control module in operative communication with the one or more processing units and configured to:
prompt to the user wearing the arm band to perform the training gesture;
receive the gesture instruction, and
alter the visual display based on the gesture instruction to display a virtual representation of the intended gesture,
wherein engagement with the VR system by the user wearing the arm band trains the control module to identify the intended gesture of the user based on the EMG data and the training gesture.

2. The apparatus of claim 1 further comprising:
the arm band including:
the plurality of housing elements defining the housing,
wherein the plurality of housing elements is modifiable to assume a predetermined weight, wherein a total weight of the arm band simulates a feeling of an assistive device prescribed for a particular user, wherein the predetermined weight is modifiable incrementally.

3. The apparatus of claim 1, wherein the arm band includes a wireless transmitter that allows for EMG information to be transmitted wirelessly.

4. The apparatus of claim 3, wherein the arm band includes a myoelectric control interface, and the wireless transmitter transmits a gesture instruction produced by the myoelectric control interface.

5. The apparatus of claim 1, wherein the arm band is wrapped around the residual limb of a user.

6. The apparatus of claim 1, wherein the arm band includes amplification and processing electronics, contained within the plurality of housing elements for processing EMG signals.

7. An apparatus for prosthetic training, comprising:
an arm band for training use of a prosthetic limb configured to be coupled to a residual limb of a user including:
a plurality of housing elements defining a housing,
one or more EMG sensors provided in at least one of the plurality of housing elements; and
one or more kinematic sensors;
one or more processing units in operable communication with the one or more EMG sensors of the arm band, the one or more processing units configured to:
receive EMG data of the residual limb from the one or more EMG sensors, predict an intended gesture of the user wearing the arm band for training use of the prosthetic limb from the EMG data; and
generate a gesture instruction in response to the user performing a training gesture; and
a virtual reality (VR) system including:
one or more detectors for motion tracking, configured to receive data from the one or more kinematic sensors to determine a position or orientation of the arm band relative to the VR system; and
a VR control module in operative communication with a VR display and the one or more processing units, said VR control module configured to prompt the user to perform the training gesture and generate instructions to control movement of a virtual reality limb displayed on the VR display based at least on the gesture instruction received from the one or more processing units.

8. The apparatus of claim 7, further comprising a flexible connector interconnecting the plurality of housing elements.

9. The apparatus of claim 7, wherein at least one of the plurality of housing elements includes the one or more kinematic sensors for tracking of an orientation of the housing.

10. The apparatus of claim 9, wherein the tracking is performed using virtual reality tracking employed by the VR system, and wherein the VR control module is in operative communication with the one or more kinematic sensors.

11. The apparatus of claim 7, wherein at least one instruction from the one or more processing units is based on the intended gesture predicted by the one or more processing units.

12. The apparatus of claim 10, wherein the instructions to control movement of a virtual reality limb are generated by the VR control module based on an input from the one or more kinematic sensors.

13. An apparatus, comprising:
   an arm band configured for prosthetic training including a plurality of housing elements, an electromyography (EMG) sensor, at least one kinematic sensor, and a processing element;
   an electromyography (EMG) control module in communication with the processing element of the arm band configured to:
      receive EMG information generated by the EMG sensor in response to movement of a residual limb of a user wearing the arm band in one or more physical dimensions; and
      identify a gesture class based on the EMG information; and
   a virtual reality (VR) system including:
      a VR display;
      one or more VR detectors configured to receive data from the one or more kinematic sensors; and
      a VR control module in operative communication with:
         the one or more VR detectors for determining a position of the arm band with respect to the VR system;
         the VR display; and
         the EMG control module,
      the VR control module being configured to prompt the user to perform a training gesture within the gesture class in each of the one or more physical dimensions and generate instructions to control movement of a virtual reality limb displayed on the VR display based at least on a gesture instruction generated by the EMG control module in response to the user performing the training gesture; and
   wherein the EMG control module is further configured to:
      train based on the gesture class and the EMG information received in response to the user performing the training gesture,
      wherein the gesture class is trained using EMG information received from user movement in each of the one or more physical dimensions, and
      wherein the EMG control module as trained is configured to provide the gesture instruction to a prosthetic device worn by the user in response to the user performing the identified intended gesture.

14. The apparatus of claim 13, wherein the EMG control module is provided as a myoelectric control interface on the arm band that receives EMG information from the EMG sensor and predicts a gesture associated with the user based on movement of the arm band.

15. The apparatus of claim 13, wherein the EMG control module is further configured to modulate a speed of actuation of the prosthetic device by using an amplitude of an EMG signal represented in the EMG information and provide an instruction to the prosthetic device.

16. The apparatus of claim 13, wherein the one or more kinematic sensors provides a proportional control value to the VR control module to control speed of the virtual reality limb displayed on the VR display.

* * * * *